Aug. 8, 1967 M. R. MULFORD Plant Pat. 2,756
PILEA PLANT
Filed June 9, 1966
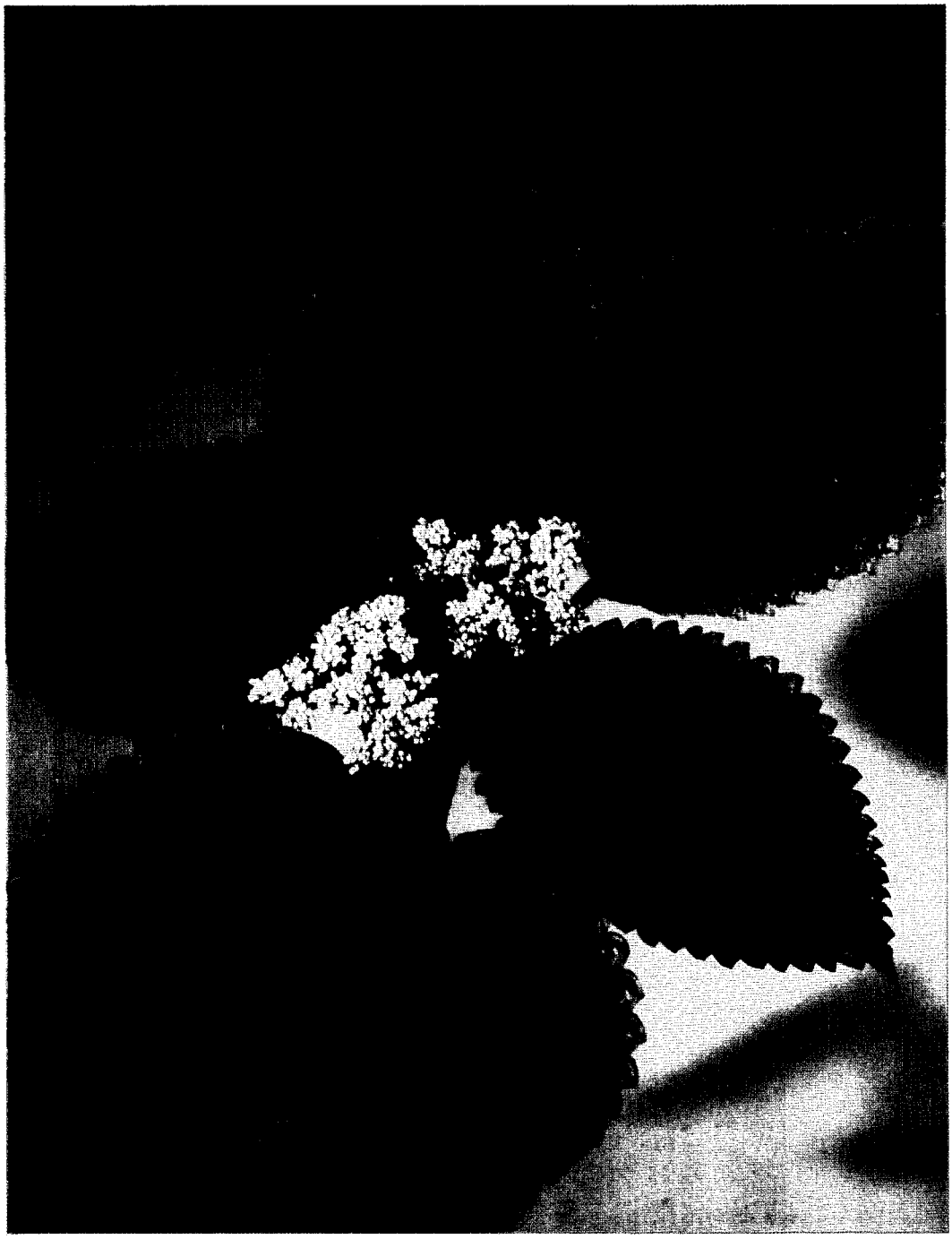
Inventor.
Marion R. Mulford
By: Robb & Robb
Attorneys.

United States Patent Office

Plant Pat. 2,756
Patented Aug. 8, 1967

2,756
PILEA PLANT

Marion R. Mulford, Altamonte Springs, Fla., assignor to Rare Plants, Inc., Altamonte Springs, Fla., a corporation of Florida

Filed June 9, 1966, Ser. No. 556,529
1 Claim. (Cl. Plt.—88)

The present invention relates to a new and distinct variety of Pilea plant which was discovered by me in the greenhouses on my property at Lebanon, Ohio, as a sport of a Pilea plant of unknown parentage which had been found by me in Central America.

At the time of my discovery of the sport aforementioned, a group of plants of the parent variety were being grown under my direction and control in the greenhouses referred to above, in the course of which my attention was attracted to the new sport because of a number of important characteristics which were substantially different from those typical of the parent variety, and which represent substantial and valuable improvements thereover that make it more attractive and desirable from a commercial standpoint, as evidenced by the following unique combination of features which distinguish the sport from its parent, as well as from all other Pilea varieties of which I am aware:

(1) A larger plant size than that of the parent variety, with mature plants attaining a height of up to 12 inches;

(2) Larger and heavier leaves than those of the parent variety, said leaves averaging from 4 inches to 7 inches in size and being more prominently roughened in a papilla-mamillate form;

(3) A distanctive and attractive leaf color ranging from light green at the edges, with darker shades of green toward the bases of the protuberances and sometimes being overlaid with reddish-brown shadings over the central portions of the leaves;

(4) Distinctive and attractive light coral pink to salmon pink colored flowers borne in clusters; and (5) Ease of reproduction by cuttings.

Asexual reproduction of my new Pilea variety, as performed by me by cuttings at Lebanon, Ohio, and also at Altamonte Springs, Fla., shows that the foregoing characteristics and distinctions are fixed and established and come true through succeeding propagations.

The accompanying drawings show a typical specimen plant of my new Pilea variety as depicted in bloom and in color as nearly true as it is reasonably possible to make the same in a color illustration of this character.

The following is a detailed description of my new Pilea variety, as based on observations of specimen plants grown at Altermonte Springs, Fla., with color terminology in accordance with Koster's Color Guide, except where general color terms of ordinary dictionary significance are obvious:

Parentage: Sport of a Central American Pilea variety of unknown parentage.

Propagation: Holds its distinguishing characteristics through succeeding propagations by cuttings.

*Plant*

Habit: Herbaceous perennial.

Growth: Low-growing; ranges in height from 8 inches to 12 inches, with an equal or somewhat greater spread; from upright to semi-spreading; much-branched; shade preferring; usually monoecious, but sometimes dioecious.

Stem: Approximately square in cross-section, but with the angles enlarged to form rather prominent ridges, with a prominent groove between each adjacent pair of ridges; glaucous except for a few scattered, inconspicuous, short (from ⅛ inch to ¼ inch long), slender, watery, semitransparent hairs; surface slightly but distinctly rugose; from about ⅛ inch to ¼ inch in diameter.

*Color.*—Pale green at first, but takes on a reddish-brown color corresponding to near Violet, Plate 59, particularly toward base, as stem ages, with more reddish-brown color than in parent variety.

*Internodes.*—Rather short (from about 1 inch to 2 inches long).

*Nodes.*—Not noticeably enlarged or swollen, but having a brownish-red line encircling the same when the stipules abscise.

Leaves: Simple; opposite; petiolate.

*Stipules.*—Short; board; inconspicuous; clasping; encircling the stem; thin-membranaceous; from obtuse to rounded; glaucous, but with hairs like those on the stem on their edges and with a few scattered on the surface; abscizing early. Color—greenish white.

*Petioles.*—From ½ inch to 1 inch long; terete except for being somewhat flattened above and slightly grooved near base; medium stout (from about 1/32 inch to 1/16 inch in diameter); glaucous except for a few inconspicuous, irregularly scattered slender, watery and semi-transparent hairs from about 3/16 inch to ¼ inch long. Color—light green, corresponding to near Reseda, Plate 85.

*Blades.*—Broadly ovate, but occasionally almost round; symmetrical; from about 4 inches to 7 inches long. Base—rounded, but varying from obtuse to slightly acute, and occasionally being slightly notched. Margin—irregularly and coarsely serrate to almost rather deeply dentate; medium thickness, but appearing very thick because of very rough surface.

*Upper surface.*—More prominently roughened than in parent variety and being papillate-mammillate instead of only savoyed-rugose; velvety; tri-nerved, with nerves deeply recessed. Color—margins near Lettuce Green, Plate 74, shading darker toward center of blade to near Spinach Green, Plate 75 between veins and having a dark green overcast near Taxus Green, Plate 81 or even darker toward base of protruding areas, while intervenal areas of main portion of blade are deep, velvety brownish-red. Veins and veinlets—deeply recessed; Color—brownish-red, corresponding to near Salmon, Plate 18.

*Under surface.*—Lighter colored than upper surface, with margins and intervenal areas corresponding to near Artichoke Green, Plate 72, with some medium brownish-red overlay somewhat lighter in shade than on corresponding areas of upper surface. Veins and veinlets—prominently protruding; Color—light green, with slight tinge of brownish-red along main nerves or veins, with veinlets being deep brownish-red corresponding to near Deep Carmine Violet, Plate 46.

Axillary buds: Extremely small and barely visible until they start to unfold into vegetative or flower structures; either vegetative or inflorescence producing; characteristically a single vegetative branch develops from an axially bud, or sometimes one, or more commonly two, inflorescences, and a vegetative shoot develops from an axil.

*Flowers*

Inflorescence: Both staminate and pistillate influorescences are cymose; pistillate ones spread out to form a flattish structure from about 1 inch to 2 inches in diameter, with rather short, slender green peduncles and peduncle branches and pedicels lacking or very short;

staminate influorescences are extremely compact, and are from the ½ inch to ¾ inch in diameter, forming what looks more like a flattish head than a cyme, and having extremely short pedicels, with green pedicels and peduncle branches.

*Color.*—Pale coral pink or salmon pink, corresponding to near Bright Rose, Plate 32.

*Pistillate flowers.*—From 3 to 6 individual flowers borne in small, almost sessile clusters in the much-branched inflorescence; from 50 to 100 individual flowers in the cyme, with each flower having a 3 or 4-parted calyx closely clasping the pistil; individual flowers approximately ⅛ inch long and nearly the same width, with inconspicuous scale-like staminodia; ovary angled in cross-section and being from narrowly ovate to ovate-lanceolate, glaucous and green in color, with sessile stigma appearing tufted and having from 5 to 10 short hair-like branches of reddish-brown color.

*Staminate flowers.*—Small (about ⅛ inch in diameter and of about the same or a little greater length), with 3 or 4 small, glaucous sepals that are shorter than the stemens; stamens being 3 to 4 in number, with almost sessile anthers that discharge their pollen explosively; there may be 40 or more staminate flowers in the inflorescence, with inconspicuous abortive pistils.

I claim:

A new and distinct variety of Pilea plant, substantially as herein shown and described, characterized particularly as to novelty by the unique combination of a larger plant size than that of the parent variety, with mature plants attaining a height of up to 12 inches, larger and heavier leaves than those of the parent variety, said leaves averaging from 4 inches to 7 inches in size and being more prominently roughened in a papilla-mammillate form, a distinctive and attractive leaf color ranging from light green at the edges, with darker shades of green toward the bases of the protuberances and sometimes being overlaid with reddish-brown shadings over the central portions of the leaves, distinctive and attractive light coral pink to salmon pink colored flowers borne in clusters, and ease of reproduction by cuttings.

No references cited.

ABRAHAM G. STONE, *Primary Examiner.*

ROBERT E. BAGWILL, *Examiner.*